United States Patent [19]

McAleer et al.

[11] 3,965,258

[45] June 22, 1976

[54] PROCESS FOR PRODUCTION OF VACCINES

[75] Inventors: William J. McAleer, Ambler; Kenneth L. Posch, Lansdale, both of Pa.; Clarence L. Baugh, Lubbock, Tex.; Raymond E. Spier, Merron Guilford, England

[73] Assignee: Merck & Co., Inc., Rahway, N.J.

[22] Filed: Apr. 16, 1975

[21] Appl. No.: 568,493

Related U.S. Application Data

[63] Continuation-in-part of Ser. No. 420,478, Nov. 30, 1974, abandoned, which is a continuation of Ser. No. 191,835, Oct. 22, 1971, abandoned.

[52] U.S. Cl. .................................. 424/89; 195/1.1; 195/1.8
[51] Int. Cl.² .................. A61K 39/12; C12B 1/00; C12K 5/00; C12K 7/00
[58] Field of Search ................ 195/1.8, 1.1; 424/89

[56] References Cited

UNITED STATES PATENTS

| 3,407,120 | 10/1968 | Weiss et al. | 424/89 |
| 3,594,277 | 7/1971 | Mako | 195/142 |
| 3,642,574 | 2/1972 | Okazaki et al. | 424/89 |

*Primary Examiner*—Sam Rosen
*Attorney, Agent, or Firm*—Donald J. Perrella; J. Jerome Behan

[57] ABSTRACT

Process for producing a live virus vaccine for the immunization of chickens against Marek's disease utilizing a multiplate machine.

7 Claims, No Drawings

PROCESS FOR PRODUCTION OF VACCINES

This is a continuation-in-part of application Ser. No. 420,478, filed Nov. 30, 1974 which, in turn, is a continuation of application Ser. No. 191,835, filed Oct. 22, 1971, both now abandoned.

This invention relates to a process for producing a vaccine against Marek's disease.

More particularly, this invention relates to a process for producing on a commercial scale a live virus vaccine for the immunization of chickens against Marek's disease.

Marek's disease has become one of the most destructive poultry diseases and has caused very substantial losses to the poultry industry throughout the world. A vaccine has recently been produced from turkey herpesvirus, which vaccine may be administered to chicks which range in age from 1 day to 3 weeks, in order to provide immunization against this disease. However, the problem associated with any veterinary vaccine, particularly a vaccine for the treatment of poultry and other small animals, is to produce the vaccine at a cost which is low enough to make it economically feasible for the poultry farmers to use the vaccine.

Present processes and equipment for producing vaccines on surfaces or substrates are not suitable for large-scale commercial production because they require the utilization of a large number of individual units, i.e., bottles, with their associated handling steps, high labor costs, and high risk of loss through contamination, in order to obtain significant amounts of vaccine. One such process for vaccine production entails cell growth on the bottom surface of many bottles. A sterile medium containing a suspension of cells is added to the bottles and the cells are incubated until a sheet of cells is formed on a submerged glass surface, after which the cell growth medium is replaced with a fresh medium containing the virus. After the virus has penetrated the cells, and the virus concentration in the medium has obtained a satisfactory level throughout the reproductive process, the virus is harvested and further processed to produce the vaccine.

The present invention provides a process for producing a live virus vaccine for the immunization of chickens against Marek's disease which eliminates the disadvantages of the prior art processes. This process involves the use of a multiplate machine as, for example, one of the type produced by Biotech A.B. of Sweden or the New Brunswick Scientific Company, which gives a higher density of cells per unit volume, requires lower volumes of media per cell, and provides a uniform, controlled environment. This process also employs pH control and glucose addition, instead of total re-feed to maintain the cells. Furthermore, according to the process of this invention, the virus may be added simultaneously or substantia simultaneously with the growth medium which further decreases the possibility of contamination and increases the efficiency of the process.

A still further advantage of the process of this invention is that the vaccine may be produced in the desired titer without any further concentration steps which may result in contamination and increased handling costs.

The machine utilized in practicing the process of this invention contains a series of titanium discs which are mounted on a rotatable shaft in a cylindrical stainless steel vessel. The vessel is capable of being placed in the upright position, in which the plating surface of the disc is in a horizontal plane to enable the cells to adhere to the surface of the titanium discs, and may then be inverted in order to enable the cells to adhere to the other side of the discs. The device is then placed on its side so that the discs may be rotated through the medium contained therein in order to produce the virus at the desired concentration.

In general, the process of this invention comprises filling the vessel with a mixture containing cells, the growth medium, and the virus; elevating the temperature of the vessel to the desired growth temperature while the vessel in in a vertical position and maintaining said growth temperature during the growth cycle; maintaining the vessel in that position for an extended period of time in order to enable the cells to adhere to the top surface of the titanium discs contained in the vessel; inverting the vessel and reincubating it in order to enable the cells to adhere to the other side of the titanium discs if two-side sticking is desired; turning the unit to a horizontal position and rotating said discs in order to continually expose the discs alternatively to the medium and the air contained in the unit above the level of the medium. The unit is aerated with an air/carbon dioxide mixture and the pH is controlled by the addition of sodium bicarbonate. Glucose may be added to the unit either intermittently or continuously and this addition may be accomplished by manual or automatic means. When the desired concentration of virus is reached, the growth medium is voided from the unit and the cells are stripped from the discs by means of a cell dispersing solution as, for example, a citrate tyrpsin solution. The resultant trypsin cell slurry may then be poured into a vessel containing fetal calf serum and this slurry is then centrifuged to obtain the vaccine, or alternatively medium may be added to the trypsin cell slurry to produce the virus suspension.

Suitable mediums include Eagles Basel Medium lactalbumin hydrolyse, Medium 199 and Eagle's Minimum Essential Medium (EMEM), while fetal calf, calf, bovine, A-gamma calf or A-gamma bovine serums may be used. Suitable cell systems include chick kidney, chick embryo fibroplast and duck embryo fibroplast cultures.

EXAMPLE 1

In a 4-liter bottle a mixture of the following is prepared:
1. 3.0 l of Eagle's Basel Medium and tryptose phosphate broth
2. 150 ml fetal calf serum
3. 3 ml penicillin, streptomycin and mycostatin
4. $3.0 \times 10^7$ cells from 12-day-old duck embryos
5. $3.6 \times 10^6$ PFU Marek's THV This mixture is pumped into the propagator while the unit is in the vertical position (plates horizontal) and the entry/exit tubes are clamped off. The unit is then inverted several times and placed in an incubator at 36°-37°C for approximately 20 hours. 1.2 Liters of medium is then voided and the unit is turned to the horizontal position. Rotation and aeration with a 95% air/5% $CO_2$ mixture is commenced and the pH is adjusted to 7.2 with 7.5% $NaHCO_3$. On the second day, 20 ml 7.5% $NaHCO_3$ is added and on the third, fourth and fifth days 10 ml of 7.5% $NaHCO_3$ is added. 1 Gram of glucose is also added to the unit on the fourth and fifth days. On the sixth day the virus is harvested by voiding the growth medium through the exit tube and adding 1.5 liters KCl-citrate trypsin to the unit. After 2–3 minutes the discs are rotated by hand to strip the cell sheet and the trypsin/cell slurry is then voided into a 4-liter bottle containing 100 ml of fetal calf serum. The trypsin/serum/cell slurry is then dispensed into 200 ml amounts in a 250 ml centrifuge bottle which is centrifuged at 100 rpm for 10 minutes.

EXAMPLE 2

The cells may be plated and grown on both sides of the titanium discs by pumping the mixture of Example 1 into the unit in the vertical position, clamping off the entry/exit tubes, inverting the unit several times and placing the unit in an incubator at 36°–37°C without disconnecting the tubing to the 4-liter bottle. After 3 hours the fluid is drained from the unit into the 4-liter bottle and $3 \times 10^9$ cells and $3.6 \times 10^6$ PFU Marek's THV is added. The mixture is pumped back into the unit and the entry/exit tubes are clamped off. The unit is then inverted to allow the cells to settle on the opposite side of the titanium plates, and is then placed in the incubator at 36°–37°C. After 3 hours 1.2 liters of medium is voided and the unit is turned to the horizontal position, whereupon the unit is rotated and further processed as described in Example 1.

EXAMPLE 3

The procedure of Example 1 is followed except that the virus is harvested by voiding the growth medium through the exit tube and adding 1.5 liters of KCl-citrate trypsin solution to the unit. The discs are then rotated to insure wetting of the entire plate and the KCl-citrate trypsin/cell slurry is voided from the unit. After 5 minutes, 1150 ml of Marek's medium containing 15% serum is added and the virus suspension is then harvested through the exit tube.

What is claimed is:

1. A large scale tank process for producing a live virus vaccine for immunization of chickens against Marek's disease which comprises
   incubating a mixture of viral-free cells, growth medium and isolated turkey herpes virus in a multi-plate apparatus which comprises a plurality of discs mounted on a rotable shaft, the incubation being started before any substantial cell growth has taken place in the multi-plate apparatus,
   continuing the incubation until a satisfactory virus level is obtained, and
   harvesting the virus.

2. A process according to claim 1 wherein the cells, growth medium and turkey herpes virus are added to the vessel substantially simultaneously.

3. A process according to claim 1 which comprises substantially simultaneously filling a multi-plate apparatus which comprises a series of discs mounted on a rotable shaft with a mixture containing cells, growth medium, and turkey herpes virus,
   incubating the mixture until a satisfactory level of virus is obtained, and harvesting the virus.

4. A process according to claim 1 wherein the incubation is started by elevating the temperature of the vessel to the desired growth temperature while said vessel is in a vertical position and maintaining said growth temperature during the growth cycle.

5. A process according to claim 1 wherein the incubation is continued by maintaining the vessel in the upright position for a time which is sufficient to enable the cells to adhere to the top surface of the discs contained in the vessel;
   turning the unit on its side and rotating said discs in order to continually expose the discs to the medium and the air contained in the vessel; and
   controlling the conditions in the vessel by aerating with an air/carbon-dioxide mixture, adding a sodium bicarbonate solution and adding glucose.

6. A process according to claim 1 wherein the vaccine is harvested by
   a. voiding the growth medium from the vessel;
   b. stripping the cells from the discs by means of a cell dispersing solution;
   c. pouring the resultant slurry into a vessel containing fetal calf serum; and
   d. centrifuging the slurry obtained in Step (c) to obtain the vaccine.

7. A process according to claim 1 wherein the incubation is continued by
   maintaining the vessel in the upright position for a time which is sufficient to enable the cells to adhere to the top surface of the discs contained in the vessel;
   adding additional cells and virus to the vessel;
   inverting the vessel for a time which is sufficient to enable the cells to adhere to the other surface of the discs contained in the vessel;
   turning the unit on its side and rotating said discs in order to continually expose the discs to the medium and the air contained in the vessel; and
   controlling the conditions in the vessel by aerating with an air/carbon-dioxide mixture, adding a sodium bicarbonate solution and adding glucose.

* * * * *